United States Patent [19]

Miyamoto et al.

[11] Patent Number: 4,610,891

[45] Date of Patent: Sep. 9, 1986

[54] PROCESS FOR SUGAR-COATING SOLID PREPARATION

[75] Inventors: Yosuke Miyamoto, Okegawa; Hajime Goto, Warabi; Hiroshi Sato, Omiya; Hiroshi Okano, Niiza; Masao Iijima, Tokyo, all of Japan

[73] Assignee: Zeria Shinyaku Kogyo Kabushiki Kaisha, Tokyo, Japan

[21] Appl. No.: 802,201

[22] Filed: Nov. 25, 1985

[51] Int. Cl.$^4$ ................................................ A61K 9/28
[52] U.S. Cl. ............................................ 427/3; 424/35
[58] Field of Search ............................... 427/3; 424/35

[56] References Cited

FOREIGN PATENT DOCUMENTS 1070808  6/1976  Japan ........................................ 424/35

*Primary Examiner*—Sam Silverberg
*Attorney, Agent, or Firm*—Scrivener Clarke Scrivener and Johnson

[57] ABSTRACT

A process for sugar-coating a solid preparation such as tablet, pill, granule or grain with a sugar-coating liquid comprising pullulan and/or a water-soluble derivative thereof dissolved in an aqueous solution of sucrose. The solid preparation sugar-coated by the above-mentioned process exhibits an enhanced impact strength and shelf life.

7 Claims, No Drawings

PROCESS FOR SUGAR-COATING SOLID PREPARATION

BACKGROUND OF THE INVENTION

This invention relates to a process for sugar-coating a solid preparation such as tablet, pill, granule or grain to thereby increase impact strength shelf life thereof.

Conventional sugar-coating liquids used in preparing sugar-coated tablets contain binders such as gelatin or gum arabic so as to increase strength of the sugar-coating layer or to increase bonding strength between an uncoated tablet and the sugar-coating layer.

However these well-known binders have various disadvantages. For example, gelatin, which has been frequently employed, might show considerable changes including browning with the lapse of time to thereby decrease the commercial value of products. It might further insolubilize the sugar-coating layer, thus retarding the disintegration of tablets. These disadvantages are considered to be caused by protein denaturation of gelatin. When gum arabic is employed, the bonding strength between the sugar-coating layer and the uncoated tablet might be insufficient, which often results in cracks in the sugar-coating layer.

In addition to these binders, it has been recently attempted to use other binders such as sodium carboxymethylcellulose, polyvinylpyrrolidone, polyvinyl alcohol, high-molecular polyethylen glycol and α-starch in sugar-coating. However these binders still have various defects in that the suspension behaviors and viscosity of the obtained sugar-coating liquid are inappropriate for coating or that the bonding strength thereof is insufficient.

DETAILED DESCRIPTION OF THE INVENTION

Under these circumstances, we, the inventors, have studied to develop a binder capable of forming an excellent sugar-coating which would show no change with the lapse of time nor retardation of the disintegration. As a result, we have found that the above object can be achieved by employing a sugar-coating liquid comprising pullulan and/or a water-soluble derivative thereof, such as a water-soluble pullulan ether or a water-soluble pullulan ester, thus completing the present invention.

Accordingly, the present invention provides a process for sugar-coating a solid preparation which comprises employing a sugar-coating liquid comprising pullulan and/or a water-soluble derivative thereof dissolved in an aqeous solution of sucrose.

The pullulan as used in the present invention, which is an extracellular viscous material obtained by culturing Pullularia pullulans, was isolated by R. Bauer for the first time in 1938. In 1959, H. Bender et al. revealed its structure as will be shown below (Biochim. Biophys. Acta., 36, 309 (1957):

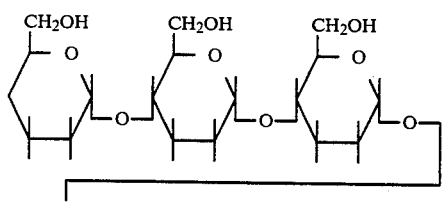

-continued

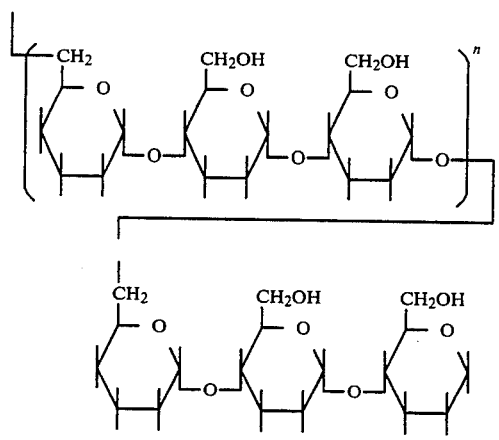

wherein n is an integer representing the degree of polymerization.

Thus pullulan is a linear natural high polymer comprising repeating units of maltotriose, which is a trimer of glucose, linked through α-1,6 bonding, different from the bonding of the trimer.

Japanese Patent Publication No. 36360/1976 has disclosed a process for increasing the yield of pullulan. Properties of pullulan would slightly vary depending on the type of the strain and culture conditions. However any type of pullulan is available in the present invention. Preferred molecular weight thereof is in the range of 10,000 to 5,000,000, though not limited thereby.

The water-soluble derivative of pullulan as used in the present invention, such as a water-soluble pullulan ether or a water-soluble pullulan ester is a derivative which is prepared by employing pullulan as the starting material and may be substituted by various radicals so far as the water solubility of the pullulan is maintained. It may be synthesized in a conventional method.

In general, a pullulan ester may be prepared by make pullulan reacting with an anhydride, chloride or ester of an inorganic or organic acid in water or in an organic solvent such as pyridine, quinoline or dimethyl sulfoxide in the presence of a catalyst such as sodium hydroxide, pyridine or sulfuric acid. Typical examples thereof are acetates and butyrates. Since the derivative used in the present invention should be water-soluble, the degree of substitution depends on the kind of substituents. For example, in the case of a pullulan acetate of a molecular weight of 150,000, those substituted by up to approximately 1.1 acetyl radicals per three hydroxyl radicals of glucose are soluble in water, whereas those having a higher degree of substitution are insoluble in water.

A pullulan ether may be prepared in a conventional method by, for example, adding small amounts of an alkaline solvent and dimethyl sulfate or diethyl sulfate to pullulan or reacting methyl iodide therewith. Typical examples thereof are methyl, ethyl and propyl ethers.

Concentration ranges of sucrose and pullulan and/or a water-soluble derivative thereof in the sugar-coating liquid as used in the present invention are 30 to 80% (W/W), preferably 40 to 70% (W/W), and 0.1 to 10% (W/W), preferably 0.5 to 5.0% (W/W), respectively. The sugar-coating liquid may contain additional agents conventionally used in sugar-coating liquids, such as pigments, binders and opacifying agents.

The sugar-coating liquid thus prepared may be used in sugar-coating a solid preparation such as tablet, pill, granule or grain in a conventional method.

A sugar-coated solid preparation prepared by the process of the present invention have a high impact strength and show little browning as well as similar disintegration behaviors as that observed immediately after its preparation even after the storage under severe conditions. Pullulan and water-soluble derivatives thereof are soluble in cold or hot water and compatible with other compounds, so that the sugar-coating liquid of the present invention can be readily prepared. Furthermore the sugar-coating process of the present invention can be efficiently carried out with the use of a single sugar-coating liquid which makes complete high-speed automation of said process possible.

To further illustrate the present invention, and not by way of limitation, the following examples will be given.

EXAMPLE 1

| composition of sugar-coating liquid | % (W/W) |
| --- | --- |
| sucrose | 62.0 |
| water | 32.0 |
| pullulan | 1.5 |
| titanium dioxide | 2.0 |
| kaolin | 2.5 |

A sugar-coating liquid of the above composition was prepared. Approximately 3,000 tablets (8 mm in diameter) each weighing 180 mg and comprising vitamins $B_2$ and $B_6$ and L-cysteine were introduced into a sugar-coating pan of 30 cm in diameter. Approximately 150 g of the above-mentioned sugar-coating liquid was poured into the pan while rotating the latter. After evenly contacting with the sugar-coating liquid, the tablets were dried by blowing hot air stream. The drying procedure was repeated and the tablets were treated in a conventional method. A sugar-coated tablet thus prepared (ca. 9.3 mm in diameter) weighed approximately 300 mg and had an excellent, white and glossy appearance.

The impact strength and changes in disintegration period and appearance with the lapse of time under severe conditions of the white tablet thus obtained were compared with those of a tablet sugar-coated with a sugar-coating liquid comprising 1.0% (W/W) of gum arabic and 0.5% (W/W) of gelatin instead of pullulan.

The impact strength of a sugar-coating layer was evaluated from the number of tablets of which the sugar-coating layer was cracked after dropping the tablets one after another through a vertical glass tube (2.5 cm in diameter × 150 cm in length) onto a glass plate. Table 1 shows the result.

TABLE 1

Number of tablets having cracked sugar-coating layer

| | Number of tested tablets | Number of cracked tablets |
| --- | --- | --- |
| Pullulan-coated tablet (Ex. 1) | 40 | 6 |
| Gum arabic/gelatin-coated tablet (control) | 40 | 25 |

Changes with the lapse of time in a sugar-coating layer were evaluated by observing the color change thereof after storing at 50° C. for two months or at 60° C. for one month. Table 2 shows the result.

TABLE 2

Browning of sugar-coating layer after storage

| | Degree of browning* | |
| --- | --- | --- |
| | 50° C./2 months | 60° C./1 month |
| Pullulan-coated tablet (Ex. 1) | − | ± |
| Gum arabic/gelatin-coated tablet (control) | ± | + + |

*−: no change observed.
±: change scarcely observed.
+: a little change observed but yet commercially available.
+ +: considerable change observed and commercially unavailable.

Changes in the disintegration period of sugar-coated tablets were evaluated by determining the disintegration periods thereof in a conventional method immediately after their preparation and after storing at 40° C. for 45 days, at 50° C. for 45 days, or at 60° C. for 30 days. Table 3 shows the result.

TABLE 3

Change in disintegration period of sugar-coated tablet with time

| | Disintegration period (min.) | | | |
| --- | --- | --- | --- | --- |
| | imm. after prepn. | 40° C./45 days | 50° C./45 days | 60° C./30 days |
| Pullulan-coated tablet (Ex. 1) | 5.0 | 5.0 | 5.2 | 5.8 |
| Gum arabic/ gelatin-coated tablet (control) | 6.5 | 8.0 | 12.0 | ≧20 |

EXAMPLE 2

| composition of sugar-coating liquid | % (W/W) |
| --- | --- |
| sucrose | 63.0 |
| water | 30.5 |
| pullulan | 1.5 |
| talc | 5.0 |

Sugar-coated tablets were prepared with the use of a sugar-coating liquid of the above composition in the same method as described in Example 1.

EXAMPLE 3

| composition of sugar-coating liquid | % (W/W) |
| --- | --- |
| sucrose | 60.0 |
| water | 32.0 |
| pullulan | 0.5 |
| talc | 4.0 |
| ppt. $CaCo_3$ | 3.5 |

Sugar-coated tablets were prepared with the use of a sugar-coating liquid of the above composition in the same method as described in Example 1.

EXAMPLE 4

The procedures of Example 2 was followed except that acetylpullulan obtained by substituting pullulan by up to approximately 1.1 acetyl radicals per three hydroxyl radicals of glucose instead of pullulan was employed.

Changes in the disintegration periods and hardnesses of sugar-coated tablets as prepared in Examples 2 and 4 were compared with those of sugar-coated tablets prepared in the same method as described in Example 2 except that the sugar-coating liquid contained 1.0% (W/W) of gum arabic and 0.5% by weight of gelatin instead of the pullulan. Tables 4 and 5 show the results.

TABLE 4

Change in disintegration period of sugar-coated tablet with time

| | Disintegration period (min.) | | |
| --- | --- | --- | --- |
| | imm. after prepn. | 60° C./10 days | 60° C./20 days |
| Pullulan-coated tablet (Ex. 2) | 4.5 | 5.0 | 5.2 |
| Pullulan-coated tablet (Ex. 3) | 4.5 | 5.2 | 5.2 |
| Acetypullulan-coated tablet (Ex. 4) | 5.0 | 5.5 | 5.8 |
| Gum arabic/gelatin-coated tablet (control) | 4.2 | 8.0 | 15.0 |

TABLE 5

Change in hardness of sugar-coated tablet with time

| | Hardness (kg)** | |
| --- | --- | --- |
| | imm. after prepn. | 60° C./10 days |
| Pullulan-coated tablet (Ex. 2) | 9.2 | 9.2 |
| Pullulan-coated tablet (Ex. 3) | 8.8 | 8.6 |
| Acetylpullulan-coated tablet (Ex. 4) | 9.4 | 9.0 |
| Gum arabic/gelatin-coated tablet (control) | 8.8 | 6.0 |

**determined by measuring the hardness of ten tablets of each type with the use of a Schleuniger 2E hardness tester and calculating the mean value.

What is claimed is:

1. A process for sugar coating a solid pharmaceutical preparation comprising coating said preparation with an aqueous solution of sucrose containing dissolved therein 0.1 to 10% (w/w) of pullulan or a water-soluable derivative thereof or mixtures there of.

2. A process according to claim 1 wherein said water-soluble derivative of pullulan is a water-soluble pullulan ether or water-soluble pullulan ester.

3. A process according to claim 1 wherein said pullulan and/or water-soluble derivative thereof has a molecualr weight ranging from 10,000 to 5,000,000.

4. A process according to claim 1 wherein said pullulan and/or water-soluble derivative thereof in said sugar-coating liquid has a concentration ranging from 0.5 to 50% (W/W).

5. A process according to claim 1 wherein said sugar-coating liquid contains at least one additional agent selected from the group consisting of pigments, binders and opacifying agents.

6. A process according to claim 1 wherein said solid preparation is in the form of tablet, pill, granule or grain.

7. A process according to claim 1 wherein said sucrose in said sugar-coating liquid has a concentration from 30 to 80% (W/W).

* * * * *